United States Patent [19]
Kaneko et al.

[11] Patent Number: 5,328,468
[45] Date of Patent: Jul. 12, 1994

[54] BALLOON FOR BLOOD VESSEL-DILATING CATHETER

[75] Inventors: Takashi Kaneko; Akira Mochizuki; Toshinobu Ishida, all of Kanagawa, Japan

[73] Assignee: Terumo Kabushiki Kaisha, Tokyo, Japan

[21] Appl. No.: 957,033

[22] Filed: Oct. 6, 1992

[30] Foreign Application Priority Data

Oct. 8, 1991 [JP] Japan .................. 3-289106

[51] Int. Cl.$^5$ ............................ A61M 29/00
[52] U.S. Cl. ...................... 604/96; 606/194; 604/104
[58] Field of Search ................ 604/96–103, 604/104; 606/191–194

[56] References Cited

U.S. PATENT DOCUMENTS

| | | |
|---|---|---|
| Re. 32,983 | 7/1989 | Levy . |
| Re. 33,561 | 3/1991 | Levy . |
| 4,093,484 | 6/1978 | Harrison et al. . |
| 4,154,244 | 5/1979 | Becker et al. . |
| 4,254,774 | 3/1981 | Boretos . |
| 4,490,421 | 12/1984 | Levy . |
| 4,906,244 | 3/1990 | Pinchuck et al. . |
| 4,908,272 | 3/1990 | Harada et al. ............ 428/412 |
| 5,053,259 | 10/1991 | Vicik ............ 428/36.91 |
| 5,071,429 | 12/1991 | Pinchuck et al. ............ 604/96 |
| 5,077,109 | 12/1991 | Lustig et al. ............ 428/36.91 |
| 5,108,415 | 4/1992 | Pinchuck et al. . |
| 5,156,612 | 10/1992 | Pinchuck et al. ............ 604/96 |
| 5,163,950 | 11/1992 | Pinchuck et al. ............ 606/192 |
| 5,189,097 | 2/1993 | LaFleur et al. ............ 525/57 |
| 5,195,969 | 3/1993 | Wang et al. ............ 604/96 |

FOREIGN PATENT DOCUMENTS

| | | |
|---|---|---|
| 0274411 | 7/1988 | European Pat. Off. . |
| 0349640 | 1/1990 | European Pat. Off. . |
| 362826 | 4/1990 | European Pat. Off. . |
| 58-188463 | 11/1983 | Japan . |

Primary Examiner—C. Fred Rosenbaum
Assistant Examiner—Ronald K. Stright, Jr.
Attorney, Agent, or Firm—Burns, Doane, Swecker & Mathis

[57] ABSTRACT

A balloon for a blood vessel-dilating catheter is fabricated from a biaxially oriented film of an aromatic polyamide or an alloy thereof. The balloon has a calculated modulus of elasticity of from 70 to 190 kg/mm$^2$. When the balloon is fabricated from an alloy of an aromatic polyamide, the alloy may contain up to 50% by weight of an aliphatic polyamide. The balloon of the invention is soft and flexible as well as dimensionally stable. Therefore, the balloon catheter has a high trackability, and may be inserted into the blood vessel without inducing any injury in the inner surface of the blood vessel. The balloon of the invention also has a good blood compatibility.

9 Claims, 1 Drawing Sheet

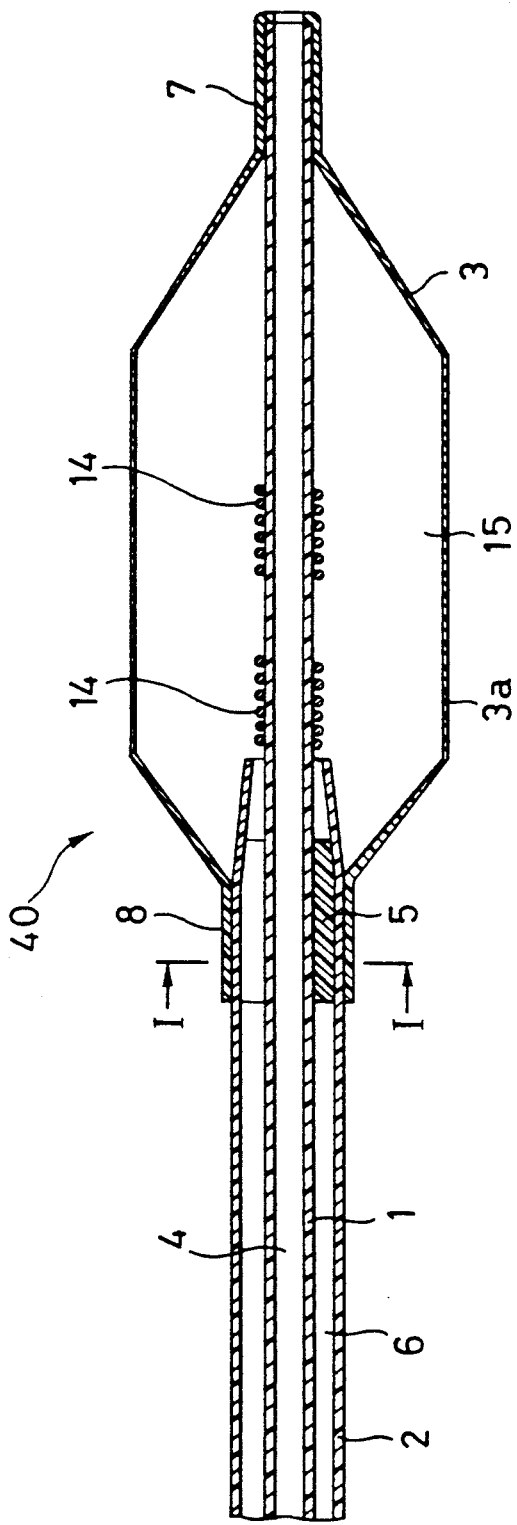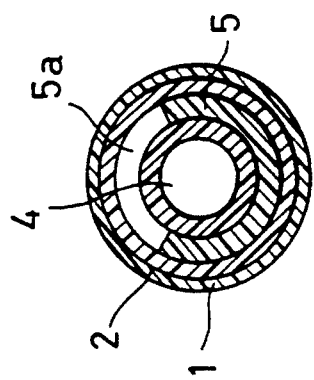

BALLOON FOR BLOOD VESSEL-DILATING CATHETER

BACKGROUND OF THE INVENTION

This invention is directed to a balloon for a blood vessel-dilating catheter.

A balloon catheter having an inflatable balloon secured at its distal end has been applied for various cavities in a living body including a blood vessel. Utility of the balloon catheter is increasing in various medical fields.

Of the balloon catheters mentioned above, a blood vessel-dilating catheter is employed in percutaneous transluminal coronary angioplasty (PTCA) to dilate a stenosis or a narrowing in a blood vessel such as coronary artery. In PTCA, the femoral artery is secured, for example, by the Serdinger method; a guiding catheter is introduced into the thus secured femoral artery and advanced through the lumen of the artery until it reaches near the target lesion, the narrowing in the artery, by manipulating a guide wire; a blood vessel-dilating catheter is introduced into the lumen of the guiding catheter to locate the balloon beyond the distal end of the blood vessel-dilating catheter; and a blood vessel-dilating fluid is introduced into the lumen of the blood vessel-dilating catheter to inflate the balloon to thereby dilate the narrowing in the blood vessel.

Such a blood vessel-dilating catheter is required to have a trackability so that the blood vessel-dilating catheter can smoothly advance through the lumen of the guiding catheter along the tortuous blood vessel to reach the lesion site. The balloon is required to have a sufficient dimensional stability as well as excellent strength and flexibility so as to avoid excessive dilatation of the narrowing of the blood vessel.

Typical balloons for balloon catheters are disclosed in U.S. Pat. Nos. 4,093,484; 4,154,244; 4,254,774; 4,906,244; and 5,108,415; and PCT Application No. JP88/00202.

The balloons described in these patents and patent application comprise a mixture of an ethylene-buthylene-styrene block copolymer and a low molecular weight polystyrene having polypropylene optionally added thereto; a composition similar to the one just mentioned wherein butadiene or isoprene is used instead of the ethylene and the buthylene; polyvinyl chloride; polyurethane; a polyester copolymer; a thermoplastic rubber; a silicone-polycarbonate copolymer; an ethylene-vinyl acetate copolymer; biaxially oriented Nylon 12; biaxially oriented polyethylene terephthalate; polyethylene; a crosslinked ethylene-vinyl acetate copolymer; etc.

The materials particularly used for the balloons of the blood vessel-dilating catheters include polyvinyl chloride (hereinafter abbreviated as PVC), polyethylene (hereinafter abbreviated as PE), biaxially oriented Nylon 12 (hereinafter abbreviated as N12), and biaxially oriented polyethylene terephthalate (hereinafter abbreviated as PET).

Among these, aliphatic high polymers such as PE, PVC, and N12 are highly flexible, realizing a sufficient trackability. These materials, however, are insufficient in their strength to detract from dimensional stability.

PET, on the other hand, has excellent strength and dimensional stability. PET, however, has an excessively high modulus of elasticity due to crystallization caused by the biaxial orientation, and therefore, is inferior in impact strength, tear resistance and flexibility, leading to poor trackability of the catheter.

Furthermore, PET is poor in coating adaptability, adhesibility, and heat sealability to suffer from insufficient operativity and workability in preparing the balloon catheter. In addition, PET inherently lacks antithrombotic properties, and it would be quite difficult to subject the PET to various treatments to impart biocompatibility, in particular, blood compatibility.

SUMMARY OF THE INVENTION

The present invention has been achieved in view of the above-described situation. An object of the present invention is to provide a balloon for a blood vessel-dilating catheter wherein the softness and the flexibility is improved without compromising the dimensional stability. Another object of the present invention is to provide a balloon for a blood vessel-dilating catheter wherein the modulus of elasticity is reduced to prevent an injury of the blood vessel inner surface, and which is blood compatible so that the catheter may be indwelled within the blood vessel for a prolonged period of time.

According to the present invention, there is provided a balloon for a blood vessel-dilating catheter fabricated from a biaxially oriented film of an aromatic polyamide or an alloy thereof, said balloon having a calculated modulus of elasticity of from 70 to 190 kg/mm$^2$.

The aromatic polyamide may preferably be a polyamide prepared by polycondensing xylylenediamine with an aliphatic dicarboxylic acid.

The aliphatic dicarboxylic acid may preferably be adipic acid.

The aromatic polyamide may preferably be a polyamide prepared by polycondensing isophthalic acid and an aliphatic diamine.

The aliphatic diamine may preferably be hexamethylenediamine.

The alloy of the aromatic polyamide may contains up to 50% by weight of an aliphatic polyamide.

The aliphatic polyamide blended in the polyamide alloy may preferably be at least a member selected from the group consisting of Nylon 6, Nylon 64, Nylon 66, Nylon 610, Nylon 612, Nylon 46, Nylon 9, Nylon 11, Nylon 12, and polyether amide.

The balloon may have a burst pressure of at least 10 kg/cm$^2$.

BRIEF DESCRIPTION OF THE DRAWINGS

FIG. 1 is a sectional view of a blood vessel-dilating catheter having the balloon of the present invention at its distal end.

FIG. 2 is a sectional view taken on line I—I of FIG. 1.

DETAILED DESCRIPTION OF THE INVENTION

PET, as described above, has a high strength, a high modulus of elasticity and a good dimensional stability, although it is poor in flexibility. PET also has a quite high melting point rendering the balloon molding difficult. On the other hand, aliphatic polymers such as PE, PVC and Nylon 12 are highly flexible, and the resulting blood vessel-dilating catheter may have a good trackability. Such aliphatic polymers, however, are poor in strength and dimensional stability, and also, suffer from decrease in their strength and dimensional alteration upon water impregnation.

In contrast, the balloon for a blood vessel-dilating catheter (hereinafter simply referred to as balloon) of the present invention comprises an aromatic polyamide, which has an excellent dimensional stability, or an alloy thereof with an aliphatic polyamide, which has an excellent flexibility and elasticity. A balloon having both excellent dimensional stability and high flexibility is thereby provided. One example of the balloon of the present invention is shown in FIG. 1.

As shown in FIG. 1, the blood vessel-dilating catheter 40 having the balloon of the present invention at its distal end consists of an inner tube 1, an outer tube 2 and a balloon 3.

The inner tube 1 has a first lumen 4 with an opening provided at its distal end. The first lumen 4 is intended to transmit a guide wire therethrough.

The outer tube 2 is intended to transmit the inner tube 1 therethrough and has its distal end provided back from the distal end of the inner tube. The inner surface of the outer tube 2 and the outer surface of the inner tube 1 form a second lumen 6. The distal end of the second lumen 6 is connected with the proximal end of the balloon 3 which will be described later, and filled with a fluid (angiographic agent, for example) for inflating the balloon 3. The distal end of the outer tube 2 is fixed to the inner tube 1 without blocking up the second lumen 6. More illustratively, as shown in FIG. 2, it is fixed by a filler 5 provided between the outer tube 2 and the inner tube 1, and the filler 5 has a partial cavity 5a, with which the second lumen 6 and the inside of the balloon 3 are connected with each other.

The balloon 3 is foldable, and can be folded around the inner tube 1 when it is not inflated. The balloon 3 has a substantially cylindrical portion 3a having almost the same diameter and at least partially cylindrical so that it can dilate a narrowing in a blood vessel with ease. The proximal end 8 of the balloon 3 is fixed liquid-tightly to the distal end of the outer tube 2, and the distal end 7 thereof is fixed liquid-tightly to the distal end of the inner tube 1 so that a dilating space 15 is formed between the inner surface of the balloon 3 and the outer surface of the inner tube 1. The proximal end of the dilating space 15 is connected with the second lumen 6 through the cavity 5a of the filler 5.

A reinforcing material 14 provided on the outer surface of the inner tube 1 is made of coil spring, and is located near the distal end of the outer tube 2 and also near the center of the balloon 3 on the outer surface of the inner tube 1 so that the position of the balloon 3 can be observed through X-raying.

Such a balloon having excellent dimensional stability as well as high flexibility may be introduced into the blood vessel with little impact against the blood vessel inner surface to prevent the blood vessel inner surface from being injured.

The reduced modulus of elasticity results in a highly flexible, soft balloon which may be easily folded to a small size with no rigid fold being formed by folding. Hard materials like PET having a high modulus of elasticity are difficult to fold into a small size due to rigid folds formed upon folding.

The balloon catheter having the balloon of the present invention secured thereto has a good trackability to follow the tortuous blood vessel and enable the balloon to reach the target lesion. More illustratively, the trackability of the balloon catheter depends not only on the foldability of the balloon to a small size but also on the flexibility of the folded balloon, namely, shell. The balloon formed of PET is poor in the flexibility of the shell to result in an inferior trackability of the catheter provided with the PET balloon. In contrast, the shell of the balloon of the present invention is soft and flexible to realize a good trackability of the catheter.

The balloon of the present invention has a good adhesion to the catheter body due to the properties inherent to the resin material. Such a good adhesion to the catheter body is quite favorable for production, and the resulting good adhesion strength between the balloon and the catheter body prevents the balloon from being peeled off from the catheter body during its storage or use.

Furthermore, the balloon of the present invention is excellent in blood compatibility, namely, antithrombotic properties due to the properties inherent to the resin material, and therefore, may be indwelled within the blood vessel for a prolonged period compared to conventional balloon catheters. In addition, since the balloon of the present invention has good compatibility with other resins as well as good coating adaptability, the balloon may be surface treated with various agents and resin coatings to realize sustained effects of the treatment.

For example, the balloon may have its exterior surface treated with various antithrombotic materials and agents to impart the balloon with a high blood compatibility for a prolonged period. The surface of the balloon may be subjected to other surface treatments for other purposes including smooth passage of the balloon through the lumen of the blood vessel filled with viscous blood, and prevention of the blood vessel interior surface from being injured by the traffic of the balloon.

Although the above-mentioned aliphatic polymers such as PE, PVC and Nylon 12 are flexible, they have low calculated modulus of elasticity and low burst pressure. On the other hand, the balloon made from the above-mentioned PET has a high burst pressure. However, once the PET balloon undergo bursting, it disrupts into numerous small pieces or debris which are quite difficult to recover. In contrast, the balloon of the present invention has a high burst pressure and would not burst even when a pressure of about 10 atmosphere is applied for expansion of the balloon, and even when the balloon should burst, it tears in a wadding configuration to enable a safe recovery.

Also, the balloon of the present invention has an impact strength higher than that of the PET balloon, and therefore, may fully endure a rapid inflation leading to safety.

The balloon for blood vessel-dilating catheter of the present composition comprises either an aromatic polyamide having a good dimensional stability, or an alloy of such an aromatic polyamide with other resin components, in particular, an aliphatic polyamide having a sufficient flexibility or elasticity. When the balloon comprises a polyamide alloy, ratio of the components may be adjusted to realize desired properties including a calculated modulus of elasticity in the range of from 70 to 190 $kg/mm^2$, and preferably from 70 to 160 $kg/mm^2$.

The term aromatic polyamide used herein designates a polyamide produced by polycondensing a diamine and a dicarboxylic acid, at least a part of the diamine or the dicarboxylic acid containing an aromatic ring.

The diamine or the dicarboxylic acid moieties containing an aromatic ring may preferably constitute from 25 to 75% by weight, and most preferably from 40 to 60% by weight of the aromatic polyamide. It is to be noted that the molar ratio of the diamine or the dicarboxylic acid moieties containing an aromatic ring to the diamine or the discarboxylic acid moieties containing no aromatic ring may not necessarily be 1:1. It is also to be noted that the aromatic polyamide may be produced by polycondensing two or more types of diamines and dicarboxylic acids.

Typical diamines or dicarboxylic acids having at least one aromatic ring include those represented by general formulae [I]:

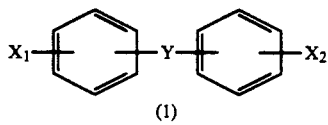

(1)

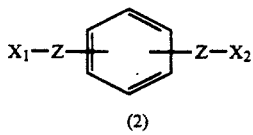

(2)

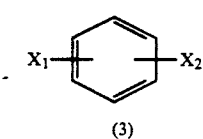

(3)

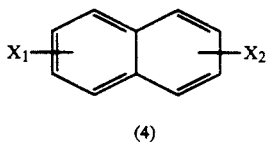

(4)

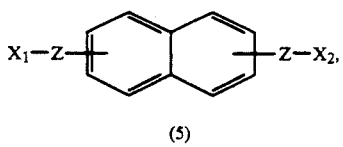

(5)

wherein $X_1$ and $X_2$ independently represent —COOH or —NH$_2$;

Y is a divalent group selected from —O—, —S—, —SO$_2$—, —(CH$_2$)$_n$— wherein n is 1 to 4, —CH(CH$_3$)CH$_2$—, —O(CH$_2$)$_n$O— wherein n is 0 to 4, —COO—, —CONH—, and —C(CH$_3$)$_2$—;

Z is a divalent group selected from —O(CH$_2$)$_n$ wherein n is 1 to 4, and —(CH$_2$)$_n$— wherein n is 1 to 4;

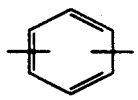

is benzene ring which may be substituted at any position; and

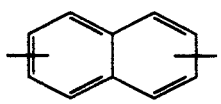

is naphthalene ring which may be substituted at any position.

Among these, those represented by formulae (2) and (3) are preferred.

Typical aliphatic diamines or dicarboxylic acids having no aromatic ring therein include diamines and dicarboxylic acids derived from a straight-chain, a branched, or an alicyclic hydrocarbon, as represented by general formulae [II]:

X$_1$—(CH$_2$)$_n$—X$_2$, wherein n is 2 to 12  (1)

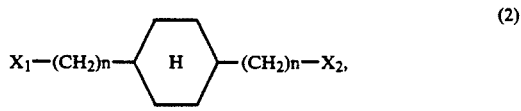

wherein n is 0 to 3

X$_1$—(CH$_2$CH$_2$O)$_m$—X$_2$, wherein m is 1 to 1,000  (3)

X$_1$—(CH$_2$CH$_2$CH$_2$CH$_2$O)$_m$—X$_2$, wherein m is 1 to 1,000  (4)

X$_1$—(CH$_2$CH(CH$_3$)O)$_m$—X$_2$, wherein m is 1 to 1,000  (5)

a dimeric acid  (6)

X$_1$—(CH$_2$C(CH$_3$)$_2$CH$_2$)$_m$—X$_2$, wherein m is 1 to 4  [II]

wherein $X_1$ and $X_2$ independently represent —COOH or —NH$_2$.

Among these, aliphatic diamines or dicarboxylic acids represented by formula (1) are preferred.

The aromatic polyamide may have a polymerization degree of approximately 50 to 5,000, and most preferably, approximately 100 to 3,000, and an average molecular weight of approximately 3,000 to 100,000, and most preferably, approximately 5,000 to 20,000.

Of the aromatic polyamides mentioned above, the most preferred in view of workability and physical properties are Nylon MXD6 synthesized from m-xylylenediamine and adipic acid and Nylon 6I synthesized from hexamethylene-diamine and isophthalic acid.

In the present invention, the aromatic polyamide as described above may be used either alone or as a main component in a polymer alloy wherein the aromatic polyamide is alloyed with a resin component having a sufficient flexibility and elasticity.

Exemplary alloying resins having a sufficient flexibility which may be used alone or in combination of two or more include thermoplastic resins such as aliphatic polyamides, modified polyolefins, polyphenylene oxides, ABS resins and polyesters. Among these, aliphatic polyamides are most preferable in view of their good compatibility with the aromatic polyamide as well as their sufficient workability.

Illustrative aliphatic polyamides which may be used alone or in combination of two or more include Nylon 6, Nylon 64, Nylon 66, Nylon 610, Nylon 612, Nylon 46, Nylon 9, Nylon 11, Nylon 12, and polyether amide.

The term, alloy or polymer alloy used herein is a concept including polymer blend, graft copolymer, random copolymer, block copolymer, and the like.

An alloying agent or a compatibilizing agent may optionally be employed in alloying the aromatic polyamide with other resins such as an aliphatic polyamide.

The resin having a sufficient flexibility, which may typically be an aliphatic polyamide, may comprise up to 50% by weight, most preferably from 0 to 40% by weight of the polymer alloy. When the flexible resin component comprises more than 50% by weight, the resulting balloon would be too poor in its modulus of elasticity and strength leading to insufficient dimensional stability.

The balloon of the present invention may be secured to the blood vessel-dilating catheter body, which may typically comprise a resin material such as polyvinyl chloride and polyethylene, by thermal fusion using a suitable heating means or with an adhesive or a solvent such as epoxy resin or cyanoacrylate adhesive. The balloon of the present invention has an excellent adhesibility with the catheter body owing to the properties inherent to the resin material, and exhibits excellent adhesion strength after securing of the balloon to the catheter body. Use of the balloon of the present invention, therefore, is quite advantageous for the production of a balloon catheter, and the thus produced balloon catheter may be safely stored and used with no risk of the balloon from being peeled off the catheter body.

The balloon of the present invention is produced by biaxially orienting the above-described aromatic polyamide or the alloy thereof wherein the the aromatic polyamide is the main constituent.

In an exemplary process for producing the balloon of the present invention, a tube or a tubular body is fabricated from the above-described aromatic polyamide or the alloy thereof wherein the aromatic polyamide is the main constituent; and the thus produced tube is axially oriented by such means as elongation or drawing. The axial orientation may preferably be carried out at an elevated temperature of, for example, from 45° to 130° C.

The thus axially oriented tube may have a length larger than its preorientation length by a factor of about 1.5 to 5.

Next, a mold having a cavity of a configuration corresponding to the balloon in its inflated state is placed over the axially oriented tube at approximately central position in its axial direction. The mold is then heated to a temperature of, for example, from 45° to 130° C. to heat the tube. The tube is inflated in its radial direction at the heated portion by applying an elevated pressure. The radius of the tube after the inflation may be about two to eight times larger than the radius of the tube before the inflation.

The heated, pressurized conditions of the tube as described above are maintained for a certain period, for example, one second to five minutes, and then, the tube is allowed to cool to approximately room temperature while the elevated pressure within the tube is maintained. The tube is thus oriented in its radial direction to form the desired balloon configuration. It is to be noted that the balloon may be subjected to repeated cycles of heat application and cooling to thereby remove the strain of the balloon.

After the cooling of the tube, the pressure is reduced to normal pressure, the mold is removed, and the balloon is trimmed to produce the balloon of the present invention.

The thus produced balloon of the present invention may have a calculated modulus of elasticity of from 70 to 190 kg/mm², and more preferably from 70 to 160 kg/mm².

A balloon having a calculated modulus of elasticity of less than 70 kg/mm² is insufficient in strength and dimensional stability. A balloon having a calculated modulus of elasticity in excess of 190 kg/mm² is insufficient in softness and flexibility leading to poor trackability of the catheter. Such a balloon also requires a high pressure for inflation, and even when inflated, the balloon may surpass its yield point and experience a plastic deformation to disenable restoration to its original configuration.

The term, calculated modulus of elasticity, E used herein is determined from a calculated tensile strength, Sc which represent the tensile strength in radial direction in film equation. The calculated tensile strength, Sc may be determined by equation [I]:

$$Sc = P \times D / 2t \qquad \text{[I]}$$

wherein
Sc is the calculated tensile strength of the film,
P is the pressure applied,
D is the initial diameter of the balloon, and
t is the thickness of the balloon.

In practice, the calculated tensile strength, Sc and the calculated modulus of elasticity, E are calculated after measuring the stress (pressure) and the strain (balloon diameter) of a balloon filled with water. Detailed measuring processes are described in Examples.

The calculated modulus of elasticity, E corresponds to the slope of the linear portion, wherein Hooke's law is applicable, of the stress-strain curve obtained by plotting the stress component (strength, Sc) in relation to the strain component (inflation of the balloon). In other words, the calculated modulus of elasticity is initial modulus of elasticity of the balloon, which may be determined by equation [II]:

$$E = \delta Sc \times D / \delta D \qquad \text{[II]}$$

wherein
E is the calculated modulus of elasticity,
$\delta Sc$ is increment in the strength,
D is initial diameter of the balloon, and
$\delta D$ is increment in the balloon diameter.

The balloon of the present invention may have a non-limited thickness, which may preferably be from 5 to 30 μm, and more preferably be from 7 to 20 μm.

Conventional PET balloons, which are provided with excellent strength and dimensional stability, are quite hard, and have a calculated modulus of elasticity of 200 kg/mm² or higher. In the present invention, the calculated modulus of elasticity has been reduced to 70 to 190 kg/mm², and preferably, to 70 to 160 kg/mm², by fabricating the balloon from the aromatic polyamide or the alloy thereof, whereby a production of a balloon provided with softness and flexibility as well as dimensional stability is enabled.

It is to be noted that the PET balloon could be imparted with a reduced modulus of elasticity by reducing the degree of orientation. In such a case, however, the stress-strain curve would exhibit a yield point, beyond which the dimensional stability as well as the strength would undergo a significant decrease. A pressurization of the balloon beyond such a yield point would lead to a plastic deformation of the balloon upon which a restoration to its original configuration and dimension would be impossible to render the withdrawal or recovery of the balloon difficult. Therefore, only a considerably limited range of-pressure could actually be employed for the PET balloon inflation.

In contrast, the balloon of the present invention is provided with sufficient softness and flexibility without compromising the dimensional stability and the strength. Accordingly, the inner surface of the blood vessel to which the blood vessel-dilating catheter is inserted is prevented from being injured by the balloon upon such an occasion as insertion of the catheter.

In addition, the balloon of the present invention, which is fabricated from the aromatic polyamide or an alloy thereof, has an excellent blood compatibility or antithrombotic property, and therefore, may be indwelled in the blood vessel for a prolonged period.

The balloon of the present invention may preferably have a burst pressure of 10 kg/cm$^2$ or higher, and more preferably, from 13 to 20 kg/cm$^2$. The pressure normally required for inflating the balloon is approximately 7 to 8 atm. The balloon of the present invention, which has a burst pressure of 10 kg/cm$^2$ or higher, would endure a more severe pressurization than such a normal pressurization, and therefore, could be successfully employed for treating a tight stenosis requiring even higher pressurization.

The present invention is described by referring to the following non-limiting Examples of the present invention as well as Comparative Examples.

EXAMPLES

Example 1

Nylon MXD6 (grade 6121, manufactured by Mitsubishi Gas Chemical Company, Inc.), which is an aromatic polyamide produced by polycondensing m-xylylenediamine and adipic acid, was molded into a tube having an inner diameter of 0.7 mm and an outer diameter of 1.1 mm. The tube was axially oriented to a length three times larger than its original length in an atmosphere at a temperature of 81° C. The tube was then placed in a metal cylinder provided with a cylindrical cavity with an inner diameter of 3 mm having opposite tapered ends. The metal cylinder was heated to a temperature of 85° C., and nitrogen was introduced into the tube to a pressure of 15 kg/cm$^2$ from its opposite ends. The tube was kept at this pressure and temperature for 15 seconds. The tube was then allowed to cool to room temperature in 1 minute with the pressure being kept at the constant level.

The metal cylinder was heated again with the pressure being kept at the constant level, but this time to a temperature of 130° C., and the tube was allowed to heat set for 20 seconds and cool to room temperature in 90 seconds.

After reducing the pressure, the biaxially oriented balloon was removed from the metal cylinder, and trimmed to obtain the balloon of the present invention. The resulting balloon had an outer diameter at its dilated portion of 3 mm and a film thickness of 15.0 μm.

Example 2

With 80% by weight of the Nylon MXD6 employed in Example 1 was blended and kneaded 20% by weight of Nylon 6 (grade 1030BRT, manufactured by Unitika Ltd.), which is an aliphatic polyamide, in a twin-screw extruder to produce MXD6/N6 alloy pellets.

A balloon was produced from these pellets in a manner similar to Example 1. The resulting balloon had an outer diameter at its dilated portion of 3 mm and a film thickness of 15.5 μm.

Example 3

With 60% by weight of the Nylon MXD6 employed in Example 1 was blended and kneaded 40% by weight of Nylon 6 (grade 1030BRT, manufactured by Unitika Ltd.), which is an aliphatic polyamide, in a twin-screw extruder to produce MXD6/N6 alloy pellets.

A balloon was produced from these pellets in a manner similar to Example 1. The resulting balloon had an outer diameter at its dilated portion of 3 mm and a film thickness of 14.3 μm.

Example 4

The procedure of Example 1 was repeated except that Nylon 6I produced by polycondensing hexamethylene diamine and isophthalic acid was used for the aromatic polyamide. The resulting balloon had an outer diameter at its dilated portion of 3 mm and a film thickness of 15.1 μm.

Example 5

With 70% by weight of the Nylon 6I employed in Example 4 was blended and kneaded 30% by weight of Nylon 6, which is an aliphatic polyamide, in a twin-screw extruder to produce N6I/N6 alloy pellets.

A balloon was produced from these pellets in a manner similar to Example 1. The resulting balloon had an outer diameter at its dilated portion of 3 mm and a film thickness of 15.3 μm.

COMPARATIVE EXAMPLE 1

A commercially PET balloon mini-profile TM USCI (manufactured by United States Catheter and Instrument) having an outer diameter at its dilated portion of 3 mm and a film thickness of 10 μm.

COMPARATIVE EXAMPLE 2

A commercially Nylon 12 balloon Cordis-Helix TM (manufactured by Dordis) having an outer diameter at its dilated portion of 3 mm and a film thickness of 8 μm.

Experiment 1: Burst Test

The balloons produced in the above-described Examples 1 to 5 and Comparative Examples 1 and 2 were subjected to a burst test. The burst test was conducted by filling the balloon with distilled water, and applying a pressure gradually increasing at a rate of 1 kg/cm$^2$ until the burst of the balloon. In this test, the balloon was recorded for its deformation in relation to the pressure applied.

In this burst test, the balloon was evaluated for its burst pressure and maximum percentage of inflation. In addition, calculated tensile strength and calculated modulus of elasticity were determined from the recorded experimental data and the dimensional measurements of the balloon by the above-mentioned equations [I] and [II]. The results are shown in Table 1, below.

TABLE 1

| | Material | Balloon | | | | |
|---|---|---|---|---|---|---|
| | | Film thickness, $\mu m$ | Calc. tensile strength, $kg/mm^2$ | Calc. modulus of elasticity, $kg/mm^2$ | Burst pressure, $kg/cm^2$ | Max. inflation, % |
| E. 1 | NMXD6 | 15.0 | 18.7 | 159 | 19.6 | 18.9 |
| E. 2 | NMXD6/N6 (80/20) | 15.5 | 18.8 | 93.2 | 20.3 | 24.3 |
| E. 3 | NMXD6/N6 (60/40) | 14.3 | 15.6 | 76.9 | 14.7 | 37.6 |
| E. 4 | N6I | 15.1 | 18.9 | 168 | 20.4 | 16.1 |
| E. 5 | N6I/N6 (70/30) | 15.3 | 16.9 | 87.0 | 18.5 | 26.5 |
| C.E. 1 | PET | 10 | 29.3 | 202 | 21.9 | 14.1 |
| C.E. 2 | N12 | 8 | 15.3 | 43.9 | 9.0 | 32.4 |

The data in Table 1 reveal that the balloon of the invention produced in Examples 1 to 5 had a calculated modulus of elasticity in the range of from 70 to 190 $kg/mm^2$, and a burst pressure of as high as over 10 $kg/cm^2$ to exhibit sufficient dimensional stability as well as satisfactory softness and flexibility.

In contrast, the balloon of Comparative Example 1 had a calculated modulus of elasticity of as high as 202 $kg/mm^2$ to exhibit poor flexibility.

In order to reduce the modulus of elasticity, a sample with a reduced degree of orientation was prepared by repeating the procedure of 1 except that a PET tube was employed and the degree of axial orientation was reduced to 2.7. The resulting balloon had an outer diameter in its dilated portion of 3 mm and a film thickness of 15.5 $\mu m$. The thus prepared balloon was subjected to the above-described burst test. The balloon had a calculated tensile strength of 16.8 $kg/mm^2$ and a calculated modulus of elasticity of 130 $kg/mm^2$. The burst pressure was 18.2 $kg/cm^2$ and the maximum inflation rate was 22.5%.

The balloon, however, exhibited a yield point stress-strain curve. When a balloon compliance, namely, the balloon diameter in relation to the pressure was measured, a significant increase in the balloon diameter was observed at a pressure of 12 $kg/cm^2$ to show that the balloon had undergone a plastic deformation after the yield point. Indeed, the balloon failed to restore its original dimension after the lowering of the pressure.

As described above, the modulus of elasticity may be reduced by such means as adjusting the degree of orientation. The resulting balloon, however, is not desirable for the purpose of the present invention since it exhibits a yield point.

The balloon of Comparative Example 2 had a low calculated modulus of elasticity of 43.9 $kg/mm^2$, and accordingly, a burst pressure of as low as 9.0 $kg/cm^2$. The pressure normally required for inflating the balloon is approximately 7 to 8 atm. Some operators, however, may conduct balloon inflation at a pressure of approximately 10 atm. or even higher. A burst pressure of less than 10 $kg/cm^2$ would therefore be insufficient.

The mode of the burst of the balloon is also a matter of interest. The balloons of Examples 1 to 5 of the present invention were axially split upon bursting, and therefore, could easily be recovered. In contrast, the balloons of the Comparative Example 1 bursted into numerous debris, which were quite difficult to recover if not impossible.

If such a bursting of the balloon burst should take place in a living body to leave unrecoverable balloon debris in the blood vessel, they may induce an extremely dangerous clogging in coronary artery as well as peripheral blood vessels. The balloon of the present invention undergo a bursting wherein an woolly residuum is left. The balloon of the present invention, therefore, could be thoroughly recovered with no significant difficulty even if the balloon should burst in a living body.

Experiment 2: Puncture Test

Film samples having a size of 150 mm × 150 mm with the film composition and thickness identical with each of the balloons of the Examples (biaxially oriented ratio 3×6) 1 to 5 were prepared to evaluate their impact strength in accordance with JIS P8134 using a puncture tester. The films exhibited an impact strength in the range of from 5 to 10 kg.cm. The test results reveal that the balloons of the present invention are provided with a sufficient safety to endure a rapid inflation.

For comparison purpose, a film sample of PET biaxially oriented to 4×4 was evaluated for its impact strength in the same manner as described above. The impact strength was 4 kg.cm. The PET balloon of Comparative Example 1 is therefore estimated to have a poor impact strength.

As set forth above, the balloon of the present invention for a blood vessel-dilating catheter is provided with excellent dimensional stability as well as sufficient softness and flexibility, leading to an improved trackability of the catheter to reach the target lesion. Injury of the blood vessel upon the introduction of the catheter into the blood vessel is also prevented.

The balloon of the present invention also has an improved adhesibility to the catheter to which the balloon is secured. This is quite advantageous for production purpose, and peeling of the balloon from the catheter is avoided.

Furthermore, the balloon of the present invention has an excellent blood compatibility, namely, antithrombotic property to enable the dwelling of the catheter in the blood vessel for a prolonged period of time. Also, the balloon of the present invention could easily be subjected to various surface treatments including coating of anti-thrombotic materials and agents on the exterior surface of the balloon.

Still further, the balloon of the present invention has a high burst pressure as well as an excellent impact strength to fully endure a rapid ballooning or inflation at a high pressure. Therefore, the balloon of the present invention is quite safe.

We claim:

1. A balloon for use with a blood vessel-dilating catheter having an inflation lumen and a second lumen, said catheter having a balloon with a proximal end fixed liquid-tightly to an outer surface of said catheter and a distal end fixed liquid-tightly to the distal end of said catheter, wherein the improvement comprises the balloon being fabricated from a biaxially oriented film of an aromatic polyamide or an alloy thereof, said aromatic polyamide having a polymerization degree of approximately 50 to 5,000 and an average molecular weight of approximately 3,000 to 100,000, said balloon having a calculated modulus of elasticity of from 70 to 190 kg/mm.

2. The balloon according to claim 1 wherein said aromatic polyamide is a polycondensation product of xylylenediamine with an aliphatic dicarboxylic acid.

3. The balloon according to claim 2 wherein said aliphatic dicarboxylic acid is adipic acid.

4. The balloon according to claim 1 wherein said aromatic polyamide is a polycondensation product of isophthalic acid and an aliphatic diamine.

5. The balloon according to claim 4 wherein said aliphatic diamine is hexamethylenediamine.

6. The balloon according to claim 1 wherein said alloy of the aromatic polyamide contains up to 50% by weight of an aliphatic polyamide.

7. The balloon according to claim 6 wherein said aliphatic polyamide is at least a member selected from the group consisting of Nylon 6, Nylon 64, Nylon 66, Nylon 610, Nylon 612, Nylon 46, Nylon 9, Nylon 11, Nylon 12, and polyether amide.

8. The balloon according to claim 1 wherein said balloon has a burst pressure of at least 10 kg/cm$^2$.

9. A blood vessel-dilating catheter comprising an inflation lumen and a second lumen, said catheter having a balloon with a proximal end fixed liquid-tightly to an outer surface of said catheter and a distal end fixed liquid-tightly to the distal end of said catheter, said balloon being fabricated from a biaxially oriented film of an aromatic polyamide or an alloy thereof, said aromatic polyamide having a polymerization degree of approximately 50 to 5,000 and an average molecular weight of approximately 3,000 to 100,000, said balloon having a calculated modulus of elasticity of from 70 to 190 kg/mm.

* * * * *

UNITED STATES PATENT AND TRADEMARK OFFICE
CERTIFICATE OF CORRECTION

PATENT NO. : 5,328,468
DATED : July 12, 1994
INVENTOR(S) : Takashi KANEKO et al.

It is certified that error appears in the above-indentified patent and that said Letters Patent is hereby corrected as shown below:

In Column 6, line 33, delete "[II(7)]" and insert --(7) [II]--.
In Column 9, line 3, delete "of-pressure" and insert --of pressure--.
In Column 11, line 37, after "point" and before "stress-", insert --in--.

Signed and Sealed this

Fourth Day of October, 1994

BRUCE LEHMAN

Attest:

Attesting Officer

Commissioner of Patents and Trademarks